US007192614B2

(12) United States Patent
Mitchell et al.

(10) Patent No.: US 7,192,614 B2
(45) Date of Patent: *Mar. 20, 2007

(54) COMPOSITIONS AND METHODS OF TREATMENT TO ALLEVIATE OR PREVENT MIGRAINOUS HEADACHES AND THEIR ASSOCIATED SYMPTOMS

(75) Inventors: Russell W. Mitchell, Schofield, WI (US); James W. Higgins, Rothschild, WI (US); Stephen C. Roberts, Minnetonka, MN (US)

(73) Assignee: GelStat Corporation, Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/457,033

(22) Filed: Jun. 6, 2003

(65) Prior Publication Data

US 2004/0086582 A1 May 6, 2004

Related U.S. Application Data

(63) Continuation-in-part of application No. 10/288,610, filed on Nov. 5, 2002, now abandoned.

(51) Int. Cl.
*A61K 36/28* (2006.01)
*A61K 36/9068* (2006.01)

(52) U.S. Cl. ..................... 424/756; 424/764
(58) Field of Classification Search ............... 424/764, 424/729
See application file for complete search history.

(56) References Cited

U.S. PATENT DOCUMENTS

| | | | |
|---|---|---|---|
| 4,379,454 A | 4/1983 | Campbell et al. |
| 4,460,372 A | 7/1984 | Campbell et al. |
| 4,758,433 A | 7/1988 | Johnson et al. |
| 5,332,577 A | 7/1994 | Gertner et al. |
| 5,384,121 A | 1/1995 | Rhodes |
| 5,503,843 A | 4/1996 | Santus et al. |
| 5,744,166 A | 4/1998 | Illum |
| 5,837,289 A | 11/1998 | Grasela et al. |
| 5,905,089 A | 5/1999 | Hwang et al. |
| 6,068,999 A | 5/2000 | Hendrix |
| 6,103,218 A | 8/2000 | Brucker et al. |
| 6,217,877 B1 | 4/2001 | Weidner |
| 6,224,875 B1 | 5/2001 | Bombardelli et al. |
| 6,299,900 B1 | 10/2001 | Reed et al. |
| 6,312,736 B1 | 11/2001 | Kelly et al. |
| 6,319,510 B1 | 11/2001 | Yates |
| 6,328,715 B1 | 12/2001 | Dragan et al. |
| 6,410,062 B1 | 6/2002 | Callaghan et al. |
| 6,444,237 B1 | 9/2002 | Heleen |
| 6,475,511 B2 | 11/2002 | Gohlke et al. |
| 6,491,940 B1 | 12/2002 | Levin |
| 6,726,939 B1 * | 4/2004 | Pak |
| 6,967,033 B1 * | 11/2005 | Spiess ................. 424/764 |

| | | | |
|---|---|---|---|
| 2001/0004644 A1 | 6/2001 | Levin |
| 2001/0021400 A1 | 9/2001 | Bombardelli et al. |
| 2002/0006987 A1 | 1/2002 | Nakayama et al. |
| 2002/0058077 A1 | 5/2002 | Shen et al. |
| 2002/0076452 A1 | 6/2002 | Babish et al. |
| 2002/0077299 A1 | 6/2002 | Babish et al. |
| 2002/0077350 A1 | 6/2002 | Babish et al. |
| 2003/0125373 A1 | 7/2003 | Nakshatri et al. |

FOREIGN PATENT DOCUMENTS

| | | |
|---|---|---|
| EP | 0553658 B1 | 1/1993 |
| EP | 1086661 | 3/2001 |
| GB | 2166952 A | 5/1986 |
| WO | WO92/11857 | 7/1992 |
| WO | WO94/06800 | 3/1994 |
| WO | WO 96/22774 * | 8/1996 |
| WO | WO98/39018 | 9/1998 |
| WO | WO 00/18415 * | 4/2000 |
| WO | WO00/62764 | 10/2000 |
| WO | WO01/45699 | 6/2001 |
| WO | WO02/09698 A1 | 2/2002 |

OTHER PUBLICATIONS www.harvestfields.netfirms.com/Tea/Info/description_uses.htm; accessed Nov. 18, 2004.*
5 pgs, Migraspray General Product Information from website: www.migraspray.com, accessed Mar. 2004.
1pg, Abstract page for Chinese Patent No. CN1372963, 2003.
10 pgs, International Search Report as issued on Apr. 2, 2004.
5 pgs, "Efficacy of feverfew as prophylactic treatment of migraine," Johnson et al., British Medical Journal, Aug. 31, 1985; vol. 291:569-573.
4 pgs, "Randomised Double-Blind Placebo-Controlled Trial of Feverfew in Migraine Prevention," Murphy et al., The Lancet, Jul. 23, 1988; 2; 189-192.
2 pgs, "Feverfew for preventing migraine (Cochrane Review)," Pittler et al., The Cochrane Library, Issue 2, 2003, www.update-software.com.
3 pgs, "Feverfew for Migraine Prophylaxis," Vogler et al., Cephalalgia 1998, www.jr2.ox.ac.uk/bandolier.
8 pgs, "Herbal Homeopathic Support for the Treatment of Migraine-Type Headache Symptoms," Blum et al., NatureWell Corporation, Aug. 29, 2001.
7 pgs, "Varietal Improvement of Herbs: Prospects and Challenges," Conrad Richter, Mar. 3-5, 1996, www.agric.gov.ab.ca/crops.
2 pgs, Nature's Nutrition—"Feverfew," product page from www.naturesnutrition.com, accessed May 2003.

(Continued)

*Primary Examiner*—Susan Coe Hoffman
(74) *Attorney, Agent, or Firm*—Kagan Binder, PLLC (57) ABSTRACT

Methods of treating migrainous headaches and their associated symptoms are provided by administering a composition comprising parthenolide or feverfew sublingually to a patient in need thereof. Treatments are surprisingly effective with low total administered amounts of parthenolide or feverfew. Compositions and unit dose systems are also described.

12 Claims, 1 Drawing Sheet

OTHER PUBLICATIONS 10 pgs, "Nuclear Factor-kB as a Molecular Target for Migraine Therapy," Reuter et al, Ann Neurol 2002; 51:507-516.

18 pgs, "Feverfew," Kemper, Longwood Herbal Task Force, Nov. 9, 1999, 1-18.

10 pgs, "Practice parameter: Evidence-based guidelines for migraine headache (an evidence-based review)," Silberstein, American Academy of Neurology 2000; 538-547.

1 pg, NatureWell, Inc.—product page from http://naturewell.com/products, accessed Jul. 2002.

2 pgs, Feverfew/Parthenolide; information page from http://www.smarteats.com, accessed Jul. 2002.

5 pgs, "The Healing Herbs," Michael Castleman, Copyright 1991, pp. 173-176.

8 pgs, "The anti-inflammatory natural product parthenolide from the medicinal herb Feverfew directly binds to and inhibits IkB kinase," Kwok et al, Chemistry & Biology, 8 (2001) 759-766.

6 pgs, "Prevalence of Migraine Headache in the United States," Stewart et al, JAMA, Jan. 1, 1992—vol. 267, No. 1: 64-69.

8 pgs, "Migraine Diagnosis and Treatment: Results from the American Migraine Study II," Lipton et al, *Headache* 2001; 41: 638-645.

5 pgs, "Migraine in the United States," Lipton et al, NEUROLOGY 43 (Suppl 3) Jun. 1993: S6-S10.

2 pgs, "Current Trends Prevalence of Chronic Migraine Headaches—United States 1980-1989", MMWR Weekly, May 24, 1991/40(20):331,337-338.

6 pgs, "Incidence of migraine headache: A population-based study in Olmsted County, Minnesota," Stang et al, Sep. 1992 NEUROLOGY 42 1657-1662.

7 pgs, "A Canadian Population Survey on the Clinical, Epidemiologic and Societal Impact of Migraine & Tension-Type Headache," Pryse-Phillips et al, *Can. J. Neurol. Sci.* 1992; vol. 19, No. 3: 333-339.

5 pgs, "Assessment of health-related quality of life in migraine," Dahlof, Cephalalgia 1993; 13:233-7.

6 pgs, "Burden of Migraine in the United States," Hu et al, Arch Intern Med/vol. 159, Apr. 26, 1999: 813-818.

7 pgs, "Tolerability and Safety of Frovatriptan with Short- and Long-term Use for Treatment of Migraine and in Comparison with Sumatriptan," Geraud et al, *Headache* 2002;42[suppl2]:S93-S99.

3 pgs, "Migraine Drug Research Heats Up As Market Soars," Brown, The Scientist 11[11]:1, May 26, 1997.

4 pgs, "Assessing and Understanding Patient Risk," Fries, Scand J. Rheumatol 1992; Suppl; 92: 21-24.

9 pgs, "Effects of ginger on motion sickness and gastric slow-wave dysrhythmias induced by circular vection," Lien et al, Am. J. Physiol Gastrointest Liver Physiol 284: G481-G489, 2003.

3 pgs, "Ginger Syrup as an Antiemetic in Early Pregnancy," Keating et al, Alternative Therapies, Sep./Oct. 2002, vol. 8, No. 5: 89-91.

7 pgs, "Ginger (Zingiber Officinale) in Migraine Headache," Mustafa et al, *Journal of Ethnopharmacology*, 29 (1990) 267-273.

5 pgs, "Feverfew as a preventive treatment for migraine: a systematic review," Volger et al, Cephalalgia, 1998; 18:704-708.

2 pgs, "Migraine Mixup," ABCNews.com, Jun. 24, 2002, American Headache Society meeting presentation by Dr. Joel Saper.

8 pgs, "Psychologic Aspects of Chronic Headache," Loretta Mueller, Journal of the American Osteopathic Association, Sep. 2000; vol. 100 (9 Suppl): S14-21.

* cited by examiner

COMPOSITIONS AND METHODS OF TREATMENT TO ALLEVIATE OR PREVENT MIGRAINOUS HEADACHES AND THEIR ASSOCIATED SYMPTOMS

This application is a continuation-in-part of U.S. patent application Ser. No. 10/288,610, filed Nov. 5, 2002, entitled "COMPOSITIONS AND METHODS OF TREATMENT TO ALLEVIATE OR PREVENT MIGRAINOUS HEADACHES AND THEIR ASSOCIATED SYMPTOMS", now abandoned, which application is incorporated herein by reference in its entirety.

FIELD OF THE INVENTION

The present invention relates to treatment of migrainous headaches and their associated symptoms. The present invention also relates to compositions, unit dose applicators, treatment regimens and compositions comprising parthenolide and/or feverfew.

BACKGROUND OF THE INVENTION

The American Migraine Study reports that 32 million Americans, 11.8% of the population; suffer with at least one migraine headache annually, and that 23 million people in the US suffer with "severe migraine" (Stewart W F JAMA 1992; 267:64–9, Lipton, RB Headache. 2001; 41:638–645). Women account for two-thirds to three-fourths of all migraine patients, as gender specific prevalence in the US is 17.6% for females and 6% for males using the IHS (International Headache Society) criteria for migraine diagnosis (Lipton RB, Neurology 1993; 43(Suppl 3):6–10). Twenty-five percent of women with migraine experience four or more severe attacks per month, 35% experience one to three severe attacks per month, and 40% experience one or less than one severe attack per month. Similar frequency patterns of migraine were observed in men (Stewart W F, JAMA 1992; 267:64–9). The overall average number of migraine attacks per year for men is 34 and 37.4 for women. In addition, "chronic recurrent headache" affects approximately 45 million Americans, the underlying pathophysiology for this condition is not yet fully understood (Meuller, L *Journal of the American Osteopathic Association*, 2000 September;100(9 Suppl):S14–21). Many researchers believe that these clinically significant headaches are primarily migraine-like (migrainous).

Headaches are one of the most common complaints heard by primary care physicians, accounting for over 10 million office visits each year in the United States. Three studies suggest that migraine prevalence may be increasing in the US (MMWR: Morbidity and Mortality Weekly Report 1991; 40:331–8; Stang P E, Neurology 1992; 42:1657–62; Pryse-Phillips W, Can J Neurol Sci 1992; 19:333–9). In fact, it may be that only the number correctly diagnosed is increasing. A very recent study of 2,524 subjects with "sinus headache" found that a full 90% were actually suffering from migraines (Saper, J. Presentation to American Headache Society, June 2002). The true incidence of migraine cannot be precisely known, but is very high.

Migraine is a severe and disabling condition. More than 85% of women and more than 82% of men with severe headache had some headache related disability (Stewart W F, JAMA 1992; 267:64–9). Approximately 33% were severely disabled or needed bed rest during an attack. Many studies have examined various aspects of headache related disability. Migraine is not just an episodic disease; it is also a chronic disease with episodic exacerbations. Many migraineurs live in fear knowing that an attack will disrupt their ability to work, to take care of their families, and to meet social obligations. Thus, there is some disability between attacks as well as during attacks. Quality of life measurements have shown that migraineurs, compared to those with other chronic illnesses, have lower scores in physical functioning and role functioning, and also experience more body pain (Dahlof, C Cephalalgia 1993; 13:233–7).

Migraine can induce a host of serious physical conditions: strokes, aneurysms, permanent visual loss, severe dental problems, coma and even death. According to the New England Journal of Medicine, "migraine can sometimes lead to ischemic stroke and stroke can sometimes be aggravated by or associated with the development of migraine." Twenty-seven percent of all strokes suffered by persons under the age of 45 are caused by migraine. Stroke is the third leading cause of death in this country. According to the Mayo Clinic, twenty-five percent of all incidents of cerebral infarction were associated with migraines. Migraine and epileptic seizure disorders are also related. The most intimate relationship between the two being migraine-triggered epilepsy. Migraine affects up to 15% of the epileptic population. In basic terms, migraine and epilepsy are both disorders characterized by short-term, fleeting alterations of neurologic function, usually with normal neurological examinations between attacks.

Finally, the economic burden of migraine indicates its severity, costing the US economy over $14 billion per year.

Economic Cost of Migraine in the US
(Hu, X Archives of Internal Medicine 1999 159: 813–8)

| Cost Element | US$ million | | |
| --- | --- | --- | --- |
| | Men | Women | Total |
| Medical | 193 | 1,033 | 1,226 |
| Missed workdays | 1,240 | 6,662 | 7,902 |
| Lost productivity | 1,420 | 4,026 | 5,446 |
| Total | | | 14,574 |

Almost all of those affected by migraine use some medicine for pain, and almost all users of prescription pain relievers are also heavy users of over-the-counter ("OTC" or non-prescription) products. U.S. consumers spend over $6 billion annually on headache pain relievers (OTC and prescription products combined). OTC products used by migraineurs, such as aspirin, acetaminophen, ibuprofen and other common analgesics, exhibit side effects associated with both chronic use and short-term overuse, which may include liver damage, kidney damage, ulcers and stomach upset. These side effects are frequently severe. Each year, use of non-steroidal anti-inflammatory drugs (NSAIDs) such as aspirin and ibuprofen, account for an estimated 7600 deaths and 76000 hospitalizations in the United States (Fries J F. Assessing and understanding patient risk. Scand J Rheumatol Suppl. 1992;92:21–4.). Frequent use of OTC analgesics has been recognized as a substantial contributor to the development of daily headaches ("chronic daily headache"). Rebound headaches are also an issue, especially with products incorporating caffeine or aspirin.

The prescription migraine market in the US for triptans alone (a class of medication frequently used to treat migraines; examples include Imitrex, Zomig, Maxalt, etc.)

was approximately $3.2 billion in 2001 (55 million prescriptions). Side effects commonly observed in this class of drugs include chest pain, shortness of breath, palpitations, paresthesias (sensation of burning, warmth, heat, numbness, tightness or tingling), asthenia (unusual tiredness or muscle weakness), dizziness, dry mouth, fatigue, hot flashes, nausea, vomiting, and sleepiness. Less common side effects include joint pain, CNS effects (agitation, anxiety, confusion, depression, irritability), eye problems (blurred vision, dry eyes, irritated eyes), chills, constipation, diarrhea, heartburn, dysphagia (trouble swallowing), euphoria, flatulence, heat sensitivity, hypertension, increased sweating, increased thirst, insomnia, muscle stiffness, muscle pain or spasms, polyuria (increased urination), pruritis (generalized itching of the skin), tinnitus (ringing in ears), tremor, vertigo, and warm or cold sensations. The fact that 55 million prescriptions are written each year in the United States for a class of drugs which cause up to 43% of users to experience adverse effects with any given dose (Geraud, G. Headache 2002 April; 42 Suppl 2:93–9) indicates the desperation of migraine patients and the need for better treatments. Total migraine prescription sales probably exceeded $4 billion and the market is growing at 4% annually (Brown, K The Scientist, 11[11]:1, May 26, 1997).

Less than half of those with migraine (48%) have been appropriately diagnosed, and only 41% of those with known migraine use prescription drugs, 57% relying exclusively on OTC medications for treatment of their migraines (Lipton, R Headache Vol 41, pp638–645, August 2001). The above study also revealed that more than half of all Americans who suffer from migraine headaches are prepared to put up with the pain rather than seek treatment from a physician, and that 26% had stopped seeing their doctor about the condition because they felt the doctor could not help. All of this suggests a heavy reliance on, even a preference for, OTC medication for the treatment of migraine. While there are no hard numbers for OTC migraine medicine sales, total OTC analgesic sales in the United States were $3.49 billion, up +2.6% vs. year prior, for the 52-weeks ending Jul. 15, 2000. OTC headache specific remedy sales were $2.65 billion, up 1.8%, on unit volume of 560 million. The fact that 57% of consumers rely entirely on OTC medications to treat a very painful, recurrent and debilitating disease demonstrates the extent of consumer preference for OTC medicines whenever available. Present OTC medications are limited in both number and effectiveness.

U.S. Pat. No. 6,103,218 to Brucker, et al., issued Aug. 15, 2000 discloses a composition and delivery system for administration of dried leaf particles of feverfew in the form of aqueous nasal spray composition. This mode of administration is stated to provide therapeutic moisturization of nasal mucous membranes, relief of migraine headaches and antispasmodic effect, such as to relieve menstrual cramping or aid digestion.

U.S. Pat. No. 6,312,736 Kelly, et al., issued Nov. 6, 2001 discloses an herbal composition for relief of pain and other symptoms associated with migraines and other types of headaches comprising: from about 46% to about 64% by weight of white willow bark extract; from about 8% to about 18% by weight of Kava Kava root extract; and from about 25% to about 41% by weight of at least one of feverfew extract and ginger root extract. The herbal composition disclosed therein is stated to be applied sublingually for rapid relief of pain.

U.S. Pat. No. 4,758,433 Johnson, et al., issued Jul. 19, 1988 discloses a preparation for pharmaceutical use, especially in the treatment of migraine, arthritis and bronchial complaints that contains a sesquiterpene lactone and is recovered from the plant *Tanacetum parthenium* by extraction using a pharmaceutically acceptable oil and is also delivered via said pharmaceutically acceptable oil, the oil being selected from the group consisting of saturated and un-saturated long chain hydrocarbons and fatty acids, vegetable and animal oils and polyoxyethylated derivatives thereof and reconstituted glycerides and esters thereof, wherein said hydrocarbon chain comprises between 10 and 25 carbon atoms, especially coconut oil, soybean oil or fish oil.

In addition to prescription and OTC medications, those with migraine headaches have attempted to treat this malady using herbal medicine or homeopathic treatments. Herbal medicine is defined as the use of herbs for their therapeutic or medicinal value. In the United States, herbal products are generally marketed as dietary supplements. An herb manufacturer or distributor can make no specific claims to diagnose, treat, cure or prevent any disease without having first obtained FDA approval. Nonetheless, information of the use of herbs for treatment of various maladies is widely available, including authoritative sources such as the Physicians Desk Reference (PDR) for Herbal Medicines, published by Thompson Medical Economics. Homeopathy is a separate theory of medical treatment, based on principles formulated by Samuel Hahnemann in the late 1700's. The practice of homeopathy is based on the belief that disease symptoms can be cured by infinitesimally small doses of substances which, in larger amounts, produce similar symptoms in healthy people. The Federal Food, Drug, and Cosmetic Act (the Act) recognizes as official the drugs and standards in the Homeopathic Pharmacopoeia of the United States and its supplements (Sections 201 (g)(1) and 501 (b), respectively).

Both feverfew and ginger have a long history of use as homeopathic and herbal remedies. Ginger has not historically been used for headache, but has been used with some success for relief of nausea. The administration of 1,000 to 2,000 mg of ginger orally by tablet has been found to effectively reduce nausea in the case of motion sickness (Lien, H C Am J Physiol Gastrointest Liver Physiol 2003 March; 284(3):G481–9). Ginger was investigated recently for its effect on nausea in morning sickness (Keating, A Altern Ther Health Med 2002 Sep–Oct; 8(5):89–91). In this study women took 1,000 mg of ginger in divided doses, the researchers concluding that ginger "may be helpful" in treatment of morning sickness. According to the Physician's Desk Reference for Herbal Medicines, the daily recommended dose of ginger for a variety of gastrointestinal symptoms (primarily various forms of nausea) ranges from 500 mg to 4000 mg. (PDR for Herbal Medicines, Thompson Medical Economics, Second Edition, *Ginger,* 339–342, 2000.) One published report suggests that ginger may be beneficial in the treatment of headache as it "has been reported in Ayurvedic and Tibb systems of medicine to be useful in neurological disorders." (Mustafa, T J Ethnopharmacol 1990 Jul;29(3):267–73). Despite this, there have been no known clinical investigations of low dose ginger, sublingual ginger or ginger in the treatment of migraines or headache in general.

Feverfew is another herb that is widely available and has been investigated in modem times. Historically, feverfew is known to have been used in the treatment of fevers, from whence it derives its name, and also in rheumatic conditions. Feverfew is used in homeopathic remedies, but homeopathy recognizes no role for feverfew in the treatment of headaches. An authoritative homeopathic text is "A Dictionary Of Practical Materia Medica" by John Henry Clarke, M.D., recognized as such by the United States Food and Drug Administration, (see the "Compliance Policy Guide: Conditions Under Which Homeopathic Drugs may be Marketed" http://www.fda.gov/ora/compliance_ref/cpg/cpgdrg/cpg400—400.html). The Clarke text gives no indication for the use of feverfew in the treatment of headaches. This same text defines the appropriate preparation of feverfew as "a tincture of fresh leaves." A tincture is a concentrated herbal extract prepared by soaking an herb in alcohol for an extended period of time. The result is an alcoholic extract referred to by homeopathic practitioners as the "mother tincture." This "mother tincture" is then subject to numerous serial dilutions with the resulting homeopathic drug being extremely dilute. Classic homeopathic remedies do not rely on any effect from the substance first contained in the starting material ("mother tincture" in this case) and often statistically contain virtually no actual molecules of the original substance (feverfew). Instead, these remedies rely on the "imprint" or "energy" of the original substance to exert an effect. Consistent with the precepts of homeopathy, the remedy thus prepared is felt to become increasingly potent, indeed stronger and more effective, as it becomes more and more dilute. Some of these homeopathic remedies may have been administered sublingually, or may yet be administered sublingually by those presently adherent to the practice. Such purported remedies would certainly contain less than 0.01 mg/ml of parthenolide and would not be employed for headache. It would be surprising to a practitioner in the art of homeopathy not only that feverfew is effective in the treatment of headache, but that the benefit not manifested at the extremely dilute concentrations employed by homeopathy is manifest by the present composition. There is little to no clinical support for any of the multitude of homeopathic remedies. Thus it is not surprising but still noteworthy that no clinical evidence exists for the effective use of feverfew in homeopathic medicine as a treatment for headache, especially as homeopathy does not recognize nor endorse this use.

Herbal medicine, as a field distinct from classical homeopathy, has in fact recognized the potential value of feverfew in the prophylactic (preventative) treatment of migraine. Fresh feverfew leaves have sometimes been chewed by subjects wishing to rid themselves of migraine. However, a common adverse effect reported by those who have used this technique is the generation sores in the mouth and sensitization of oral tissues. Additionally, many patients find this mode of administration to be crude and unpleasant. The concentration of feverfew administered by this method, even accounting for substantial dilution by the salivary juices, would remain far in excess of that employed in the present invention. The feverfew would in fact need to be diluted 1:100 by salivary juices to reach the maximum concentration employed in the present invention. In addition, the dosages historically and presently employed far exceed those of the present invention. In addition, the role of feverfew leaves in the treatment of migraine has always been restricted to prophylaxis (prevention), never having been applied to the acute treatment of headaches.

In addition to raw leaves, feverfew tablets or capsules have been and are employed by practitioners of herbal medicine. These are widely available in any "health food store" for purchase by the general public. The PDR for Herbal Medicines lists migraine, arthritis, rheumatic diseases and allergies as the indications for feverfew usage (PDR for Herbal Medicines, Thompson Medical Economics, Second Edition, *Feverfew*, 306–309, 2000.) Several studies published in leading medical journals, including "Lancet" (Murphy, J J *Lancet* 1988 Jul. 23;2(8604): 189–92), and "The British-Medical Journal" (Johnson, E S *British Medical Journal* 1985 Aug 31;291(6495):569–73), have suggested a potential role for feverfew in reducing the incidence and/or severity of migraines. The Murphy study administered one capsule of feverfew leaves to be swallowed by the patient, wherein each capsule contained about 2.19 micromoles of parthenolide (about 0.5 mg). The Johnson study administered two capsules of freeze dried feverfew powder every morning. The daily dose was therefore 50 mg feverfew. The parthenolide content of this feverfew powder was not reported. Patients reported a reduction in the number and/or severity of migraine attacks, with no side effects reported by either study. Most recently however, several systemic reviews of feverfew use in the prevention of migraine have been published (Vogler B K, "Feverfew as a preventive treatment for migraine: a systematic review." Cephalalgia 1998 Dec; 18(10):704–8) and (Pittler M H, "Feverfew for preventing migraine." Cochrane Database Syst Rev 2000;(3):CD002286) both of which reviews concluded that the efficacy of feverfew for the prevention of migraine "has not been established beyond reasonable doubt." Pittler also noted that "the trial with the highest methodological quality, which was also among the largest, found no significant difference between feverfew and placebo." Most clinicians in the United States do not consider feverfew an effective prophylactic treatment for migraine and as such do not endorse its use. Feverfew has not been used for the acute relief of migraine attacks. Each of the studies investigated only its prophylactic use. The use of feverfew acutely, for relief of headaches once they have begun, has not been studied and there is no scientific literature that directly suggests that it might be effective. In addition, the prophylactic effect is not said to be noticeable for some number of weeks (2–12) after having first initiated use of feverfew, regardless of the form of feverfew employed (tablets, leaves, etc.). Recommended dosages of feverfew tablets or capsules are 200 to 250 mg one to three times daily, there being no suggestion that alternate routes of administration or lesser doses might prove beneficial. Quite to the contrary, manufacturers generally emphasize the benefits of larger doses of feverfew. Again, neither the PDR For Herbal Medicines nor any other available herbal literature suggests the use of feverfew sublingually or as treatment of acute migraine attacks, it being believed that feverfew is wholly ineffective by such application for this purpose, or by any application for acute treatment.

A product currently available on the market is sold under the name MigraSpray®, which is stated to be a patented over the counter homeopathic drug intended to be a comprehensive approach for the treatment and prevention of migraine headaches. MigraSpray contains the active ingredients feverfew, polyporus, goldenseal and dandelion. MigraSpray is sprayed under the tongue (sublingual administration), which promotes enhanced bioavailability and rapid absorption by directly entering the bloodstream through the mucous membrane avoiding degradation from exposure to the gastrointestinal tract and liver. Product literature claims that this sublingual delivery system allows MigraSpray to provide rapid relief from migraine headache pain and other associated symptoms in an average of less than 7 minutes. However, this product, like other products sold as "homeopathic" treatments, delivers an extremely low dosage of feverfew. The amount of parthenolide reported to be present in this composition is 0.0112 mg/dose.

Additionally, it is noteworthy that the content of parthenolide in feverfew may vary to a great extent depending on the particular variety of *Tanacetum parthenium* plant grown, and also the manner of processing the feverfew herb. Parthenolide has been found to be unstable and sensitive to processing. Thus, the collection and processing steps carried out incorporating feverfew into a product may reduce or destroy the parthenolide content of the feverfew. Without a standardization of the parthenolide content of feverfew used in the process and careful control of the manufacturing process, great inconsistency is observed in parthenolide content from batch to batch of product.

SUMMARY OF THE INVENTION

It has been found that migrainous headaches and their associated symptoms may be treated by administration of a surprisingly small amount of parthenolide, and more preferably a small amount of feverfew extract, when said treatment is sublingually administered as an aqueous composition. The present invention has been found to be effective both as an acute (abortive) treatment and as a preventative (prophylactic) treatment. The combination of the correct dosage of active ingredient, together with the correct route of administration for these compositions results in a surprising degree of effectiveness for patients in need of acute and/or preventative treatment of migrainous headaches. Thus, surprisingly a material that has been administered to people for many years in various forms with widely varied effect on some maladies has been found to be as or more effective than prescription medication in the treatment of migrainous headaches when provided in compositions as described herein and administered using methods as described herein.

More particularly, the present invention provides a method of treating migrainous headaches and their associated symptoms, comprising sublingually administering an aqueous liquid composition comprising parthenolide to a patient in need thereof in a total amount of from about 0.05 mg. to about 1.0 mg. of parthenolide in a two hour period. For purposes of the present invention, a "dose" is a predetermined aliquot of composition having a predetermined amount of active ingredient contained therein. Multiple doses may be administered to a patient at about the same time, with each unit being administered considered a separate dose. In another embodiment of the present invention, a plurality of doses of parthenolide are sublingually administered over a 24 hour period, the total amount of parthenolide being about 0.05 mg. to about 1.0 mg. In this embodiment, preferably the individual doses of parthenolide each do not exceed about 0.20 mg. Preferably, the parthenolide is administered in one to six doses in a 24 hour period.

For purposes of the present invention a composition is considered to be "aqueous" if it contains water in an amount sufficient to act as the solvent for the parthenolide and/or feverfew solute. Preferably, water is present as the majority component of the composition. More preferably, water is present at an amount of from about 30% to about 99.9% of the total composition, and most preferably from about 50% to about 99% of the total composition. The compositions of the present invention are aqueous because it has been found that such compositions readily deliver the desired active ingredient systemically to the patient in a rapid manner. Additionally, aqueous compositions are generally more acceptable to the patient organoleptically during administration of the composition sublingually. Small amounts of oil may be incorporated in the composition as some trace amount of oil remains as a component of an herbal extract, and also particularly when such incorporated oils are oils that enhance the flavor of the composition. Preferably, the composition comprises no more than about 5%, and more preferably no more than about 2% oil by weight.

In a preferred embodiment of the present invention, migraine headaches and/or their associated symptoms are treated by administering a liquid composition comprising feverfew sublingually to a patient in need thereof in a total administered amount of from about 4 mg. to about 40 mg of feverfew extract in a two hour period. In another embodiment of the present invention, a plurality of doses of feverfew extract are administered sublingually over a 24 hour period, the total amount of feverfew extract not exceeding about 40 mg. Preferably, the individual doses of feverfew extract each does not exceed about 10 mg. In a preferred embodiment, the feverfew extract is administered in one to six doses in a 24 hour period.

It has also been found that the efficacy of the composition is enhanced when the composition is a liquid having an acidic pH, preferably at a pH of from about 2.5 to about 6.0. It has additionally been found that the efficacy of the composition in enhanced when the composition has a viscosity greater than water, and more preferably when the composition has a viscosity greater than about 100 cP. Compositions having higher viscosity have been found to enable the patient to better establish and maintain contact of the composition with the sublingual area. It has also been surprisingly found that such composition and treatment is effective in providing very rapid relief from migrainous headaches and their associated symptoms. In another embodiment of the present invention, the carrier liquid includes a mucosal permeation enhancer.

In one aspect of the present invention, preferably, each occurrence of a migrainous headache may be treated in a single dose as described above. The treatment as described herein may be administered for the acute relief of a migrainous headache and its associated symptoms, from any time beginning with the first sign of impending migraine headache through such time as the migrainous headache is well underway. For certain individuals the first sign of an impending migrainous headache may be other than the first mild pain. Approximately 10% of those suffering migraine headaches experience classic migraine aura, most often changes in visual perception which are unique, and which the sufferer has learned to associate with impending migraine. Classic aura may also involve other senses, with or without visual sensations, such as a unique smell. Other individuals may realize that migraine onset is imminent by the occurrence of unusual aches, pains, or merely by subjective observation of their own mood or irritability.

In a particularly preferred aspect of the present invention, the treatment may also be used daily as a prophylactic treatment, or as needed as a prophylactic treatment. In a particularly preferred embodiment of the present invention, the individual user is administered a total administered amount of the composition as described herein in response to the occurrence of a predetermined event that that individual has identified as being associated with a higher incidence of migraine for them personally. Examples of such events include menstruation, climate changes, air travel, and the like. This prophylactic administration has been found to be surprisingly effective in preventing or minimizing the onset and occurrence of migrainous headaches and their associated symptoms. Surprisingly, the treatment may additionally be used to treat headaches associated with and resulting from the consumption of alcohol.

In one aspect of the present invention, convenient systems for administration of parthenolide, and as another embodiment, feverfew extract, are provided wherein compositions are provided in a unit dose applicator for sublingual administration. More particularly, a unit dose applicator and composition for sublingual treatment of patients is provided comprising a dispenser for dispensing liquids having a reservoir and a delivery spout. The dispenser has a liquid capacity of about 0.1 to about 10 mls. This dispenser is provided with a liquid composition disposed therein. The composition comprises parthenolide in an amount not exceeding about 1.0 mg. In another embodiment, the liquid composition in the unit dose dispenser comprises feverfew extract in an amount not exceeding about 40 mg.

Liquid compositions are also provided, wherein the composition comprises parthenolide in an amount of from about 0.01 mg/ml to about 0.40 mg/ml, and more preferably from about 0.01 mg/ml to about 0.08 mg/ml. In another embodiment, the liquid composition comprises feverfew extract in an amount of from about 1 mg/ml to about 10 mg/ml.

DETAILED DESCRIPTION

It has surprisingly been found that administration of a very small amount of parthenolide, and more preferably feverfew, sublingually provides excellent treatment for migraine headaches and their associated symptoms, including acute relief of migraine headaches and their associated symptoms as well as prevention of the onset of migraine headaches and their associated symptoms. Because the active ingredients of the present composition are administered at a very low level, there is advantageously no need to obtain a prescription for use of this composition as an effective treatment of migraine headaches. The ability to effectively treat migraine headaches and their associated symptoms using such low yet rapidly effective doses of active ingredient provides substantial benefits, including not only effective relief from migraine headaches and their associated symptoms, but also the drastic reduction in side effects which might otherwise be associated with said active ingredient. By far the most commonly reported side effect of feverfew use is the occurrence of mouth sores, primarily associated with chewing feverfew leaves, wherein it may be observed in up to 11% of such users. Mouth sores are occasionally accompanied by general inflammation of tissues in the mouth. Infrequently reported side effects of feverfew use include gastrointestinal side effects such as abdominal pain, indigestion, flatulence, diarrhea, nausea, and vomiting. Some users have reported that when daily use is stopped suddenly after long periods of use, rebound headaches may occur, along with anxiety, sleep disturbances, and muscle stiffness or pain (collectively referred to as "post-feverfew syndrome," reported to occur in about 10% of migraine patients who abruptly stop taking feverfew after a long history of daily use). While most side effects are mild, it is nonetheless advantageous to avoid or reduce their occurrence to the greatest extent possible while still employing an effective dose. The methods and compositions of the present invention thus may provide an improved safety profile that may make the present invention most suitable to the average user, and particularly suitable for those with whom additional caution need be exercised, such as those who are sensitive to various medications or in the case of pediatric use, where additional cautions are generally warranted. The invention is particularly beneficial to those patients concerned about using large amounts of medication for treatment of ailments, and also to patients who wish to avoid the use of prescription medications, or who cannot afford the use of prescription medications. The low total administered amount of active ingredient and relatively small amount of total composition that is applied sublingually may additionally be of particular benefit to those treating acute migraine. This is because nausea and vomiting are frequently associated symptoms of migraine, making it often unpleasant and sometimes difficult or even impossible to administer medications in solid form or by way of larger volumes of liquids. The preparation is further beneficial to those wishing to employ migraine prophylaxis from time to time without the need to maintain daily intake of medication indefinitely.

As a new OTC medication, the present invention provides substantial benefits to migraineurs, not least of which may be the cost savings associated with a decreased reliance on expensive prescription medications and the reduction in the economic burden of migraine in the United States. There are also substantial advantages for those individuals who choose to rely on OTC medications for relief of migraine headache, namely the availability of another treatment option that may be more effective than currently available OTC products, or which may be associated with fewer side effects than currently available OTC products.

Some migraine headaches are preceded by aura or other symptom, whereby treatment of the symptom may prevent the further development of the migraine headache. The present invention provides surprisingly rapid relief, so that certain patients may avoid full onset of migrainous headaches and their associated symptoms through immediate administration of the present treatment upon onset of this symptom. In addition, many associated symptoms of migraine are found to be relieved, such as nausea, vomiting, photophobia and phonophobia (excessive/extreme sensitivity to light in one case and sound in the other). There is a growing body of knowledge which suggests that headache exists along a spectrum, with no rigid demarcation between "migraine" and "non-migraine," and that many headaches previously thought to be "not migraine" are in fact "migrainous." This may explain the fact that the present invention has been found to be effective in the treatment not only of headaches experienced by those not having been previously diagnosed with migraine, and whose headaches may not specifically qualify as migraine per the presently accepted diagnostic criteria of the International Headache Society, but also headaches not so diagnosed, including as but one example those associated with excessive alcohol use (e.g. "hangovers").

Presently known products are generally slow in providing relief, and may often exhibit undesired side effects. Surprisingly, the present invention provides rapid relief of symptoms—generally beneficial effects of the treatment are felt within minutes of administration. Prior treatments may be effective for some patients, but not for others, necessitating a lengthy and sometimes costly search by each person for the treatment that will be effective for that particular individual. Surprisingly, the present invention is effective for a large percentage of people who try this treatment. Thus, the present invention provides additional substantial benefit to the practitioner or individual who may discover conveniently and without delay those for whom this treatment is effective, searching amongst other alternatives in those cases where this medication proves insufficiently effective.

As noted above, preferably, migrainous headaches may be treated by administering a liquid composition comprising parthenolide sublingually to a patient in need thereof in a total administered amount of about 0.05 mg to about 1.0 mg of parthenolide in a two hour period. More preferably, the total administered amount is from about 0.050 mg to about 0.7 mg of parthenolide, and most preferably, the total administered amount is from about 0.08 mg to about 0.6 mg of parthenolide in a two hour period.

Additionally, there is a growing desire to use naturally generated ingredients to provide treatments for disorders. Therefore, a particularly preferred embodiment of the present invention comprises administration of small quantities of feverfew extract. More specifically, a preferred method of treating migraine headaches comprises sublingually administering a liquid composition comprising feverfew extract to a patient in need thereof in a total administered amount of from about 4 mg to about 40 mg of feverfew extract in a two hour period. More preferably, the total administered amount is from about 4 mg to about 20 mg of feverfew extract, and most preferably the total administered amount is from about 4 mg to about 12 mg of feverfew extract in a two hour period.

Feverfew extract is derived from the feverfew plant (*Tanaecetum parthenium*), which is also known, for example, as *Chrysanthemum parthenium, Chrisanthemum parthenium, Pyrethrum parthenium, Tanacete parthenii herba* or *folium, Matricaria parthenoides, Matricaria parthenium, Leucanthemum parthenium, Matricaria parthenium,* Spanish pellitory, Featherfew, Featherfoil, featherfully, and by a number of common names, various of which are used throughout the world (Midsummer daisy, Bachelor's buttons, Altamisa, nosebleed, flirtwort, ague plant, devil daisy, feddygen fenyw (Welsh), maid's weed, Missouri snakeroot, mutterkaut (German), prairie-dock, vetter-voo, wild chamomile, grande camomille (French), Santa Maria (Spain), febrifuge plant.) The extract may be obtained by techniques known in the art using solvents such as petroleum spirits or polar organic solvents. See U.S. Pat. No. 5,384,121 to Rhodes, and also WO 94 06800; EP 0 553 658; WO 92 11857; GB 2,166,952; EP 98 041; WO 98 39018.

The extract of the feverfew plant contains parthenolide, and may additionally contain other components such as Polyynes, Flavonoids and Volatile oils including camphor, borneol and others, each of which may contribute to the therapeutic effect of the preparation disclosed herein. Feverfew also contains relatively large quantities of sesquiterpene lactones, primarily parthenolide.

In addition to parthenolide, feverfew is known to contain the following non-ubiquitous chemicals: 1-Beta-hydroxyarbusculin, 10-Epicanin, 8-Beta-reynosin, Apigenin-7-glucoside, Chrysanthemolide, Chrysanthemonin, Chrysartemin-A, Chrysartemin-B, Cosmosiin, L-Borneol, L-camphor, Mangoliolide, Reynosin, Santamarin, Tanaparthin, Tanaparthin-1-alpha, 4-alpha-epoxide, Tanaparthin-1-beta,4-beta-epoxide, tenetin 3-b-hydroxyparthenolide, seco-tanaparthenolide A, canin, artecanin, and balchanin.

Because feverfew extract may contain additional beneficial components, compositions comprising the extract of feverfew are generally preferred for use in the present invention as compared to compositions comprising a highly purified parthenolide that has been isolated from the additional components naturally occurring in feverfew extract. Preferred embodiments of the present invention use feverfew extract that has been standardized to contain a predetermined standardized parthenolide concentration of preferably not less than about 1.0%, and more preferably from about 1.2% to about 10%. Higher concentration parthenolide compositions may become readily available, which may advantageously reduce the amount of liquid required in the composition for delivery of the active to the user. While the source of parthenolide in compositions of the present invention is preferably feverfew as discussed above, it may alternatively be obtained from any number of other plant species, where it generally occurs in substantially lower concentrations. Such plant species include especially other members of the Compositae family, which include especially the many species of chrysanthemums, daisies, marigolds, chamomile, yarrow and aster. Parthenolide can also be obtained from tansy. Alternatively, parthenolide may be made by any appropriate synthetic route.

The composition to be used in the present invention may optionally comprise additional active ingredients. These active ingredients may also be provided as a treatment of migrainous headaches or may provide other physical benefits, provided that the treatment benefit of parthenolide and/or the feverfew extract is not adversely affected. In one aspect, preferably additional amounts of already present sesquiterpene lactones or additional sesquiterpene lactones are incorporated in the compositions of the present invention. Preferred such sesquiterpene lactones include especially those which are known to be contained in (naturally occur in) feverfew, such as 3-Beta-hydroxyparthenolide, seco-tanaparthenolide A, canin, artecanin, chrysanthemonin, chrysartemin A and B, santamarin and balchanin, as well as those occurring in other plant species such as encelin, leucanthin B, enhydrin, melampodin A, tenulin, confertiflorin, burrodin, psilostachyin A, costunolide, guaianolide, cinerenin, artemisinin, aristolactone, lactarorufin A, bilobalide, helenalin, furandiol. Sesquiterpene lactones in addition to parthenolide may be isolated from plants such as dandelion, burdock, butterburr, mugwort and sunflower plants, among others.

Compositions to be used in the present invention may optionally additionally comprise other naturally occurring components and extracts, including those as identified in the HPUS. Preferred additional components are extracts indicated for use in treatment of headaches, inflammation, nausea or anxiety. Particularly preferred additional components are the extracts of ginger and/or green tea, or the isolated components thereof. A particularly preferred isolated component of green tea is L-theanine.

Particularly preferred compositions of the present invention contain substantially no active ingredients other than those that are extractable from herbal sources. In a particularly preferred embodiment of the present invention, the compositions contain substantially no active ingredients other than those that are extractable from feverfew, ginger and green tea sources. In another particularly preferred embodiment, the compositions contain substantially no active ingredients other than those that are extractable from feverfew and ginger. Such compositions additionally may comprise non-pharmacologically active ingredients, such as thickeners, carrier liquids and flavorants. It has surprisingly been discovered that the use of only active ingredients that are extracted from herbs provide particular benefit to the user in being both effective in the treatment of migrainous headache, and also providing natural healing conditions particularly suited to the well being of patients. Surprisingly, these natural ingredients have been found to be effective in the indicated dosage ranges when administered in a sublingual regimen as described herein. Such compositions contain parthenolide in the amounts as discussed earlier, and preferably contain less than about 400 mg of any given natural active ingredient per dose.

In particular, the combination of feverfew extract together with ginger extract is particularly effective in providing relief from migrainous headaches when provided and administered as taught herein. It has been observed that the combination of these extracts in the present compositions in particular provide synergistic effect in relieving both the pain and the nausea and/or general discomfort associated with migrainous headaches that is beyond a mere additive effect of these extracts. Incorporation of additional herbal extracts in amount as indicated herein, when delivering the composition as a sublingual aqueous administration, also provide excellent total beneficial effects of the composition exceeding what would be expected from the herbal and homeopathic literature.

In a particularly preferred embodiment, the composition to be used in the present invention additionally comprises ginger extract at a total administered amount preferably not exceeding about 400 mg, and more preferably not exceeding about 250 mg of ginger extract in a two hour period. Particularly preferred compositions comprise ginger extract as about 0.1–10% of the total composition.

In another particularly preferred embodiment, the liquid composition additionally comprises L-theanine, either as an isolated component or as a constituent of green tea extract, but in either case at a total administered amount preferably not exceeding about 400 mg of L-theanine in a two hour period. Particularly preferred compositions comprise L-theanine as about 0.1–10% of the total composition.

The liquid compositions as described herein are formulated using a carrier liquid appropriate for administration to the sublingual region of the mouth. The carrier liquid preferably is selected from water, alcohol, polyethylene glycols, glycerin, propylene glycol, and mixtures thereof. Most preferably the carrier liquid comprises water.

Thickening agents are preferably incorporated in compositions of the present invention. The thickening agent preferably assists in retention of the liquid composition sublingually for a time sufficient to allow absorption of the active ingredients in by the patient. Thickening agents are particularly desirable in sublingual applications, as a more viscous agent is more easily retained in the proper area. A more viscous agent further reduces the user's involuntary impulse to swallow, in this case perhaps prematurely. Thus, the thickening agent may assist in providing sublingual liquid retention for a time appropriate for proper absorption of the active ingredient by the patient, and also thereby may improve the clinical efficacy of the composition. Any appropriate thickening agent may be used in the composition of the present invention. Preferred such thickening agents include agar, alginate, carageenan, carboxymethylcellulose, cellulose, chitosan, corn starch, Danish agar, dextrin, furcelleran, galactomannans, gelatin, gellan gum, guar gum, gum acacia, gum arabic, gum ghatti, gum tragacanth, hydroxypropyl methylcellulose, karaya gum, methylcellulose, polyvinyl alcohol, carboxyvinyl polymer, polyvinylpyrrolidone, hyaluronic acid and salts thereof, modified starches, mucilage, pectin, potato starch, rice starch, starch, tara gum, vegetable starch, wheat starch, and xanthan gum and combinations thereof.

Most preferably, the compositions of the present invention have a viscosity that is from about 100 cP (somewhat lower than the viscosity of Olive Oil) to about 50,000 (i.e. the viscosity of molasses), and more preferably from about 500 cP (the viscosity of SAE #10 motor oil) to about 5000 cP (approximately the viscosity of Corn Syrup), all measured at 25° C.

The compositions as described herein may further comprise suitable adjuvants, such as preservatives (for example, sodium benzoate, sorbic acid and esters of p-hydroxybenzoic acid), stabilizers, antibacterial agents (such as benzyl alcohol or methyl paraben), antioxidants (such as ascorbic acid or sodium bisulfite), chelating agents (such as ethylenediaminetetraacetic acid), buffers (such as acetates, citrates or phosphates), agents for the adjustment of tonicity (such as sodium chloride or dextrose), dyes, colorants, thickening agents, flavorants, sweetening agents, and suspending agents.

In a particularly preferred embodiment of the present invention, the compositions of the present invention are provided in combination with a mucosal permeation enhancer appropriate for enhancing the mucosal absorption of the composition employed. The mucosal permeation enhancer preferably comprises azone, sodium glycholate, sodium cholate, sodium taurocholate, sodium taurocholate plus EDTA, deoxycholate, sodium lauryl sulfate, lauric acid, ethanol, lysophosphatidyl choline, polysorbate 80, cyclodextrin, cetylpyridinium chloride, cetyltrimethylammonium bromide, benzalkonium chloride, sodium salicylate, sodium EDTA, aprotinin, dextran sulfate, linoleic acid, labrafil, transcutol, urea, methoxysalicylate, POE 23 lauryl ether, various surfactants and other mucosal permeation enhancers and combinations thereof. Most preferably, the mucosal permeation enhancer comprises sodium lauryl sulfate.

In a particularly preferred embodiment of the present invention, the compositions of the present invention are provided at a pH of from about 2.0 to about 6.5, more preferably at a pH of from about 2.5 to about 6.0, and more preferably at a pH of from about 3 to about 5. Surprisingly, it has been found that compositions having a pH of the range indicated above are much more effective than compositions outside of the indicated range. Various pH adjusters may be used to adjust the pH of the composition to the desired level. Examples of suitable pH adjusters include hydrochloric acid, citric acid, phosphoric acid, acetic acid, tartaric acid, sodium hydroxide, potassium hydroxide, sodium carbonate, sodium hydrogen carbonate, boric acid, sodium borate, and the like. Preferably, the pH of the composition is adjusted to be acidic using ascorbic acid.

Preferably, the composition is buffered by a pharmaceutically acceptable buffer. Examples of buffering agents include borate buffers, citrate buffers, phosphate buffers, tartarate buffers, acetate buffers, carbonate buffers, and amino acid salts, etc. Most preferably, the buffer is sodium citrate.

Preferably, the liquid composition comprises 0.05%–10% feverfew extract, 0.1–10% ginger extract, 0.1–10% L-theanine, and 10–98% water. Preferably, the feverfew extract has a standardized parthenolide concentration of not less than about 1.0%, and more preferably from about 1.2% to about 10%.

When used for sublingual administration, compositions as described herein may be administered using any appropriate technique, such as by use of a medicine dropper, syringe, vial, or the like. Most preferably, the aqueous composition is administered in a controlled manner as a flow of liquid, rather than as a spray. A flowing liquid dispenser provides benefits of controlled delivery of the liquid to the desired position in the mouth, enhancing the likelihood that the composition to be dispensed is properly delivered. Preferably, the composition is administered using a unit dose applicator that is a dispenser having a reservoir and a delivery spout and having a liquid capacity of about 0.1 to about 10 mls. In a preferred embodiment, the unit dose applicator is provided as a dispenser having parthenolide in an amount not exceeding about 1.0 mg, or other limited quantities as discussed above. As an alternative preferred embodiment, the unit dose applicator is provided as a dispenser having feverfew extract in an amount not exceeding about 40 mg, or other limited quantities as discussed above.

Figure 1:
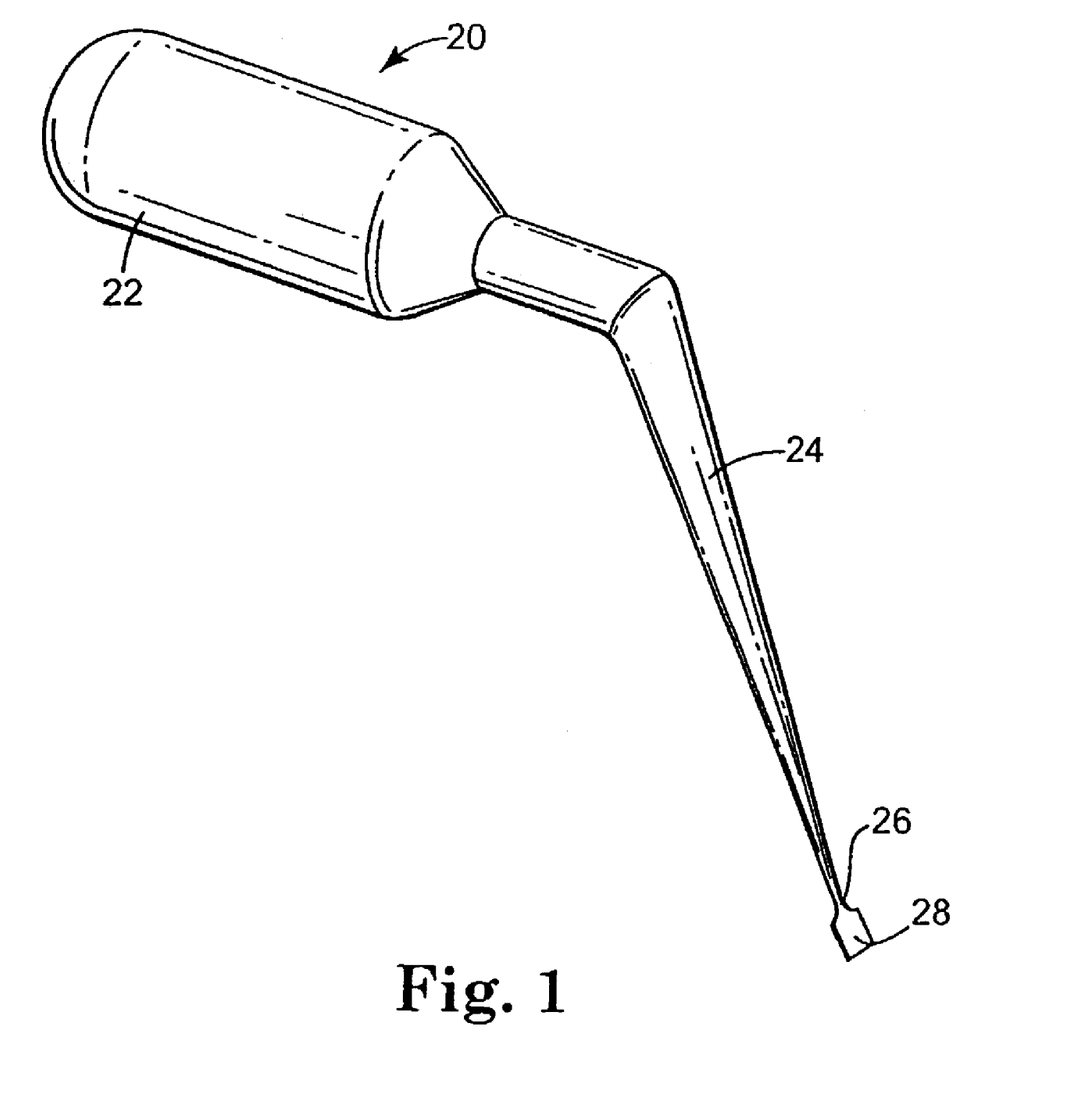
FIG. 1. shows a preferred dispenser for administering composition of the present invention.

For further clarity regarding a preferred embodiment of the present invention, FIG. 1 shows a preferred dispenser 20 for administering a single sublingual dose of the feverfew-containing composition for acute treatment of migraine. The dispenser 20 may be made with a flexible bulb, ampule, bladder, or other hollow body 22 for containing a liquid preparation that is to be administered sublingually. A tubular spout or stem 24 may be fashioned to provide a conduit through which the liquid preparation may flow when the flexible hollow body 22 is squeezed between the fingertips of the person administering the migraine treatment. The stem 24 may be formed integrally with the hollow body 22 and may be configured to taper toward the fluid outlet 26. The stem 24 may be angled to facilitate positioning the outlet 26 beneath the tongue when the medication is being administered. A break-away seal 28 may be affixed to the outlet 26 upon completion of the process of filling the dispenser 20. The seal 28 may be made by heat welding the outlet 26 or any other process. The dispenser may be made from any suitably flexible material such as polyethylene, polypropylene, nylon, or other polymer suitable for use with food and drug materials and which may be sealed after filling under sterile conditions or alternatively will withstand post-process sterilization.

A person may administer the feverfew-containing composition for treatment of migraine by breaking the seal 28 of the dispenser 20, positioning the outlet 26 of the stem 24 beneath the tongue of the patient, and then squeezing the hollow body or bulb 22 between the fingers. Squeezing the bulb 22 will cause the medication to flow through the outlet 26 into the patient's sublingual region.

A particularly preferred dispenser is the MicroDose™ dispenser commercially available from Unicep Packaging, Inc., Sandpoint, Id. Alternatively, the dispenser may be an ampule designed to mate with a plunger of a syringe to facilitate controlled delivery of the composition, such as described in U.S. Pat. No. 6,328,715.

In use of a composition of the present invention, a person in need of treatment administers the composition as described herein sublingually in an amount preferably not exceeding about 1.0 mg of parthenolide, or alternatively, not exceeding about 40 mg of feverfew extract. Preferably, the composition is administered as a plurality of sublingual applications in order to maximize effective uptake of the active ingredient by the patient, for example, for those whose headache may require more composition than can be conveniently administered in one application for its effective or entire relief.

Most preferably, the composition is administered as a first sublingual application of a first composition comprising not exceeding about 0.5 mg of parthenolide, or alternatively, not exceeding about 20 mg of feverfew, which first composition is held in place under the tongue for a predetermined time, preferably about 30 seconds, or more preferably about 60 seconds or more, after which the composition is swallowed. Most preferably, the composition is circulated or "swished" around the mouth by the patient prior to swallowing. Surprisingly, this apparently minor addition to the procedure noticeably increases the effect of the composition in the treatment. A second composition not exceeding about 0.5 mg of parthenolide, or alternatively, not exceeding about 20 mg of feverfew, is then applied and held under the tongue for a predetermined time, preferably about 30 seconds, or more preferably about 60 seconds or more, after which the second composition also is swallowed. Again, preferably the composition is circulated or "swished" around the mouth by the patient prior to swallowing. Alternatively, the total administered amount not exceeding about 1.0 mg of parthenolide, or alternatively about 40 mg of feverfew extract, may be divided among three or more compositions for sequential application as described above. This divided dosage administration technique of course may be utilized in the alternative modes of administration sublingually as described herein.

As an alternative to the unit dose applicator preferentially utilized as described above, a bottle designed so as to dispense only a certain, measured dose may be used. Alternatively, the composition may be provided in a conventional bottle with instructions to measure a dose, with or without a dedicated appliance for so doing (e.g. cup, syringe). Alternative delivery vessels that do not deliver premeasured quantities of liquid lack the advantages of convenience and higher probability of administration of the correct amount of the composition, but may be more economical than delivery of the composition using a unit dose system.

The invention will further be described by reference to the following non-limiting representative of some of the examples.

EXAMPLES

Example 1

A 26 year old African American female in otherwise good health had suffered for years with consistently recurring migraine headaches, frequency approximately 1–3 times per month, average duration 4–12 hours, which headaches had proven refractory to standard pharmacological treatment. These migraine headaches were often accompanied by nausea, and infrequently by vomiting. Each occurrence of migraine headache rendered the individual unable to participate in the normal activities of daily living, both socially and professionally. Absenteeism from work and missed social engagements resulted from her frequent need to ensconce herself in a darkened, quiet room where she would 'wait out' the headache. The frequency and unpredictability of the migraine headaches caused substantial impairment even between events, this impairment associated with anxiety and the inability to plan any event with confidence. This individual used the present invention in a two (2) part sublingual administration regimen, wherein a first composition is administered sublingually, and allowed to reside under the tongue for a period of about sixty (60) seconds. A second identical composition is administered, following the start of administration of the first composition by approximately five (5) minutes. The first and second compositions each are 2.0 ml fluid composition, which composition contained: 4 mg feverfew standardized to 1.2% parthenolide (therefore 0.024 mg parthenolide), 12.5 mg ginger and 62.5 mg L-theanine, as well as Sorbitol, Glycerin, Carrageenan, Ascorbic Acid, and Potassium Sorbate buffered with a sodium citrate buffer at pH 4.0. The viscosity of said composition having been estimated at approximately 25 cP. This individual therefore receives a total dose comprising 4.0 mg feverfew, 0.048 mg parthenolide, 25 mg ginger and 125 mg L-theanine. By using this composition as described, this individual found she obtained rapid, sufficient relief from her migraine headache and associated symptoms so as to be able to continue on with her normal activities of daily living. She reports that she continues to use the product, continues to experience similar relief, and especially appreciates the speed with which the product takes effect, and the fact that she can conveniently carry an amount sufficient for a single treatment in her purse, and thus with her at all times.

Example 2

A 32 year old Caucasian female known to experience infrequent but severe migraine headaches used the composition in Example 1 in the manner described therein for treatment of a single migraine headache. The subject reported that within 20 minutes she felt a "tingling" which she said was similar to that she generally experienced with the use of a prescription migraine medication, Imitrex, and as such she "knew it was working." She told how the migraine headache was completely resolved within one hour. This individual normally presents at an emergency room with each occurrence of migraine headache, (for treatment with Imitrex) but in this instance felt no need to access emergency room medical care.

Example 3

A 39 year old Caucasian female reported that she nearly always experienced a monthly migraine in association with her menstrual period. Menstrual migraine is reported to be especially difficult to treat, with standard pharmacological agents being of less effect, presumably because of the sustained nature of the hormonal changes acting to 'trigger' the migraine headache. This woman administered a composition, as in Examples 1 and 2 above, except lacking both ginger and L-theanine (4 mg feverfew and thus 0.024 mg parthenolide per 2.0 ml composition, resulting in a 4 mg feverfew and thus 0.048 mg parthenolide total dose). She found this composition to be of marginal effect in relieving the headache pain and associated symptoms of migraine. This individual was subsequently provided with the composition containing in addition to feverfew both ginger and L-theanine, as in Examples 1 and 2 above. This composition was administered in the two part administration regimen as described above. The subject found this composition, to be substantially more effective in relieving the headache pain and associated symptoms of migraine, reducing her described "severe" headache pain to "mild" pain, while eliminating most of the nausea and vomiting she was frequently used to experiencing with these menstrually associated migraines.

Example 4

A 23 year old female college student reported consistently experiencing an "aura" beginning approximately 15 minutes before the first onset of migraine headache pain. This subject has found that by employing a composition as in Examples 1 and 2 above, except lacking both ginger and L-theanine (4 mg feverfew and thus 0.024 mg parthenolide per 2.0 ml composition, resulting in a 4 mg feverfew and thus 0.048 mg parthenolide total dose) at the time of aura will successfully abort these migraine attacks. Whereas aura was "always" followed by migraine headache, treatment with the feverfew composition, containing neither ginger nor L-theanine, is surprisingly effective at relieving migraine by "always," as reported by this individual, preventing its occurrence as a full-blown attack.

Example 5

A 45 year old male physician reported a history of migraine headaches. A first composition was employed comprising 1.5 ml of fluid, each ml containing 1 mg of feverfew standardized to 0.7% parthenolide in the two part application regimen as described above, thus providing administration of a total of 3.0 ml of fluid and 3 mg of feverfew (0.021 mg parthenolide). This subject reported no relief when using this composition.

This individual experienced "substantial" relief when the composition was modified such that 2.0 ml doses were substituted, each containing 2 mg of feverfew standardized to 1.2% parthenolide, thus a total of 4.0 ml of fluid, 4 mg of feverfew, 0.048 mg parthenolide being administered. The effectiveness of this modification is in part surprising because it runs contrary to the tenets of homeopathy, wherein more dilute preparations are said to exert greater beneficial effects. We have found that more dilute preparations are less beneficial and in particular that dilutions of less than the dosage ranges as described herein are substantially less beneficial and perhaps even not beneficial at all.

Furthermore, this individual experienced yet greater benefit through the addition of ginger and L-theanine and adjustment of the composition pH to approximately 4.0 as provided for in Example 1, such that, when employing the composition as described in Example 1 above, his relief from migraine headache pain and associated symptoms is nearly entire.

Example 6

A 19 year old Caucasian female who is a college student and in otherwise good health but plagued by chronic migraine headache, with headaches occurring approximately six times per month, has had moderate success with treatment using Imitrex, which relieves most of the pain and associated symptoms of migraine headache. Nonetheless, this individual does not like the side effects associated with her use of Imitrex, primarily a feeling of "weakness" and "exhaustion" which follows Imitrex use and remains for some hours, usually at least the remainder of a day. Also, she is limited in her access to the prescription medication. Her medical insurance only pays for two Imitrex treatments per month and she cannot afford the cost of using Imitrex on each occurring migraine headache. This individual used a composition consisting of two (2) compositions administered sublingually as herein provided, administration of the second composition following administration of the first by approximately five (5) minutes. Each composition comprised 2.0 ml of fluid which 2.0 ml of fluid contained: 4 mg feverfew standardized to 1.2% parthenolide, and therefore 0.024 mg parthenolide. This individual therefore received a total dose of 4.0 mg feverfew (0.048 mg parthenolide associated therewith). By using this composition as described, this individual found she often obtained rapid, sufficient relief from her migraine headache and associated symptoms, without subsequent "weakness" and "exhaustion." As a result, she was able to significantly reduce (by over 50%) her use of Imitrex, and values the composition for use as a 'first-line' medication with the ability to follow its use by Imitrex, her usual prescription medication, in those instances where she obtains insufficient relief by way of the present invention.

Example 7

A 52 year old Caucasian female in generally good health used the present invention to treat a particularly severe headache. Specifically, the two part treatment regimen as described in Example 1 was employed using a composition comprising 2.0 ml of fluid containing: 4 mg feverfew standardized to 1.2% parthenolide (therefore 0.024 mg parthenolide), 12.5 mg ginger and 62.5 mg L-theanine. This individual therefore received a total dose of 4.0 mg feverfew, 0.048 mg parthenolide, 25 mg ginger and 125 mg L-theanine. This individual has never been diagnosed with migraine headache, but when she was seen had extreme headache pain on only one side (unilateral) which was pulsatile in nature, both of which symptoms are classic for migraine headache. The pain was of such severity that the woman was crying when seen. Shortly after using the composition, the woman reported that, while she still had very mild headache pain, nonetheless she "felt like her old self" and felt as though she could enjoy the remainder of her evening.

Example 8

A 21 year old Caucasian male university student who seemed to be in otherwise good health reported that he had experienced severe, intermittent headaches from a young age, and had just recently been diagnosed as having migraine headaches. He was given several samples of the composition of Example 7 for use, and later reported that his experience with the composition was "excellent," that it relieved his headaches quickly, and that he had not noticed any side effects from the medication. This individual is very involved in athletics and had chosen not to take any prescription medication because of his concerns regarding side effects, especially diminished athletic performance. He has requested a continuing supply of the composition.

Example 9

A 37 year old Asian female reports a long history of consistent and predictable migraine headache always associated with her menstrual period. This woman uses the composition of Example 7 as a migraine preventative by administering one 2 ml dose per day beginning two days before her anticipated first day of menstruation and continuing through the fourth day after the onset of menstruation. Whereas this individual first reported that she had "experienced a migraine headache with every single menses for the past several decades," she now reports several months without the occurrence of the usual, menstrually associated migraine headache.

Example 10

A 40 year old Caucasian woman who has frequent and moderately severe migraines has consistently found relief using the composition of Example 7 (feverfew standardized to contain 1.2% parthenolide). Relief from migraine headaches with the composition comprised of feverfew standardized to contain 1.2% parthenolide was always relatively rapid, generally being obtained in 30 to 45 minutes, but never sooner. In addition, while the subject was very pleased with the relief provided, some residual mild headache seemed nearly always to remain. Upon using the same composition, except having feverfew standardized to contain 4.0% parthenolide, the woman reports much faster relief, her migraine headaches now resolving in a matter of less than 10 minutes, and sometimes in as little as 5 minutes. In addition, this higher parthenolide containing composition provided nearly complete relief of migraine headache pain when also provided as a substantially thickened composition (estimated at approximately 1000 cP.) While many have reported such speedy and entirely efficacious relief from the composition employing 1.2% parthenolide feverfew and without such substantial thickening, it appears that some gain additional benefit by means of these variations of the composition.

Example 11

A 48 year old Caucasian male reported that he frequently experienced migraine headaches after having traveled in commercial airliners (after flying). He subsequently began using the composition by administering one 2 ml dose of the composition of Example 7 approximately 30 minutes prior to air travel. He reports that since beginning such use of the composition, he has not had any experience of migraine headache following air travel. This individual appreciates the fact that the composition can be used as a migraine preventative in this way, whereas all other such preventative medications he is aware of require continuous daily use.

Example 12

Many individuals have reported that compositions of the present invention, both with and without either or both ginger and L-theanine, quickly relieve many of the symptoms of a "hangover" resulting after excess consumption of alcohol, especially the symptoms of headache and associated nausea.

Clinical Evaluation #1

A clinical evaluation was undertaken to determine the efficacy of a product of the present invention as an acute treatment for relief of migraine headache pain and associated symptoms among subjects with moderate to severe migraine headache pain. This study was a double-blind, randomized, parallel group, single migraine, placebo controlled single site study.

In this study, 19 moderate and severe migraine subjects treated a migraine headache with two consecutive 2.0 ml. doses of medication (contents of each unit dose applicator=2.0 ml.). Subjects were randomized into one of two groups, with one group receiving placebo (6 subjects) and the other receiving active medication of the same formula as that of Example 1 (13 subjects).

Subjects were randomized to either active or placebo control groups. Study subjects treated one "eligible migraine" as defined by the study protocol with the medication (active or placebo) provided. The full contents of one unit dose applicator were applied sublingually, held in place under the tongue for 60 seconds, then swallowed. The second dose was taken five (5) minutes after the first dose was completed, having been administered in exactly the same way. Subjects were instructed to wait until their migraine headache pain became moderate to severe before initiating treatment. Results of this study are presented in Table 1, below.

TABLE 1

|  | Negative Response | Positive Response | % Response | Response within 1 hour | % Response within 1 hour | Pain Free at 2 hours | % Pain Free at 2 hours | Total Subjects |
|---|---|---|---|---|---|---|---|---|
| Active Medication (n = 13) | 5 | 8 | 62% | 7 | 54% | 4 | 31% | 13 |
| Placebo Control (n = 6) | 4 | 2 | 33% | 1 | 17% | 1 | 17% | 6 |

The composition of the present invention was found to significantly effective in relieving acute migraine pain and associated symptoms as well as preventing worsening of the headache pain as compared to a placebo.

TABLE 2

|  | Sumatriptan (Imitrex) | Zolmitriptan (Zomig) | Composition Of Example 1 |
|---|---|---|---|
| 1 Hour headache response | 20% | 44%[1] | 54% |
| 2 Hour headache response | 59% | 66%[2,3,4] | 62% |
| 2 Hour complete headache response[5] | 36% | 40–45%[6,7] | 54% |
| 2 hour pain free | 29% | 27–33%[8] | 31% |
| 2 hour sustained pain free | N/A | 31%[9] | 31% |

[1] http://www.zomig.com/professional_html/details/abs_rapoport.asp The headache response rates with zolmitriptan doses > or = 2.5 mg were 44 to 51% at 1 hour, 65 to 67% at 2 hours, Optimizing the dose of zolmitriptan (Zomig, 311C90) for the acute treatment of migraine. A multicenter, double-blind, placebo-controlled, dose range-finding study. The 017 Clinical Trial Study Group. Rapoport AM, Ramadan NM, Adelman JU, Mathew NT, Elkind AH, Kudrow DB, Earl NL. Neurology. 1997 Nov;49(5): 1210–8.
[2] http://www.zomig.com/professional_html/details/fast.asp In this placebo-controlled 2-attack study, headache response was achieved in 16.5% of attacks as early as 30 minutes (placebo, 12.5%; P = .048), increasing to 59% of attacks at 2 hours (placebo, 30.6%; P < .0001) when treated with ZOMIG-ZMT 5 mg[1]
[3] http://www.zomig.com/professional_html/details/abs_rapoport.asp The headache response rates with zolmitriptan doses > or = 2.5 mg were 44 to 51% at 1 hour, 65 to 67% at 2 hours, Optimizing the dose of zolmitriptan (Zomig, 311C90) for the acute treatment of migraine. A multicenter, double-blind, placebo-controlled, dose range-finding study. The 017 Clinical Trial Study Group. Rapoport AM, Ramadan NM, Adelman JU, Mathew NT, Elkind AH, Kudrow DB, Earl NL. Neurology. 1997 Nov;49 (5):1210–8.
[4] http://www.zomig.com/professional_html/details/abs_solomon.asp Headache response at 2 hours was 62% for zolmitriptan compared with 36% for placebo. Clinical efficacy and tolerability of 2.5 mg zolmitriptan for the acute treatment of migraine. The 042 Clinical Trial Study Group. Solomon GD, Cady RK, Klapper JA, Earl NL, Saper JR, Ramadan NM. Neurology. 1997 Nov;49(5):1219–25
[5] http://www.zomig.com/professional_html/details/lasting.asp Data on file, AstraZeneca Pharmaceuticals LP, DA-ZOM-11. Unpublished data.
[6] http://www.zomig.com/professional_html/details/lasting.asp Data on file, AstraZeneca Pharmaceuticals LP, DA-ZOM-11. Unpublished data.
[7] http://www.zomig.com/professional_html/details/abs_5mgStudy.asp The sustained response (2-hour headache response with no recurrence or rescue medication for 24 hours) was 43% in the zolmitriptan 5 mg ODT group. Zolmitriptan orally disintegrating tablets shows significant efficacy as early as 30 minutes, and high sustained response rates: results of a large placebo-controlled trial [poster] Speirings EL, Dodick D, Pearlman EM, Abu-Shakra S. Presented at: 14th Annual Migraine Trust; London; Sep. 23–26, 2002.

TABLE 2-continued

|  | Sumatriptan (Imitrex) | Zolmitriptan (Zomig) | Composition Of Example 1 |
|---|---|---|---|

[8] Overall, pain-free response at 1 hour postdose was achieved in 10.6% of attacks treated with ZOMIG-ZMT 5 mg compared to 4.4% for placebo (P = .0002); at 2 hours postdose, 31.1% of attacks treated with ZOMIG-ZMT 5 mg became pain free compared to 11% for placebo (P < .0001)[1] Unpublished data.
[9] Among attacks treated with ZOMIG-ZMT 5 mg, a sustained pain-free response at 24 hours was achieved in 22.2% of attacks compared to 8.2% for placebo (P < .0001)[1] also unpublished data, see same web address as for #5

Clinical Evaluation #2

A clinical evaluation was undertaken to determine the efficacy of a product of the present invention as an acute treatment for relief of migraine headache pain. This study was an open label, single migraine study. In this study, 29 moderate and severe migraine subjects treated a migraine headache with two consecutive 2.0 ml. doses of medication (contents of each unit dose applicator=2.0 ml.). The medication had the same formula as that of Example 1.

The composition was administered as follows: The liquid from one ampule is applied sublingually (under the tongue), held in place for 60 seconds, and then swallowed. The liquid from the second ampule is administered in an identical manner, but follows ingestion of the first by five (5) minutes. Subjects who were not pain-free within 60 minutes after administration of the first two ampule administration repeated the 2 ampule administration in the same manner as above. Results of this study are presented in Table 3, below. Of the 24 subjects below with mild or no pain at 2 hours, 16 used the second set of two consecutive 2.0 ml. doses of medication, and 8 of these 16 appeared to derive additional benefit from the second set of two consecutive 2.0 ml. doses of medication. Those having used both the first and second set of two consecutive 2.0 ml. doses of medication would thus have administered a total of 8 mg feverfew comprised of 0.096 mg parthenolide.

TABLE 3

| Total Subjects | Pain is mild or none at 2 hours | | Never exceeded mild pain | | Pain free at 2 hours | |
|---|---|---|---|---|---|---|
|  | Number | Percent | Number | Percent | Number | Percent |
| 29 | 24 | 82.8% | 18 | 62.1% | 14 | 48.3% |

In this study, the composition of the present invention was found to be effective in relieving acute migraine pain and associated symptoms as well as preventing worsening of the headache pain.

All patents, patent documents, and publications cited herein are incorporated by reference as if individually incorporated. Unless otherwise indicated, all parts and percentages are by weight. The foregoing detailed description has been given for clarity of understanding only. It will be appreciated that numerous modifications and variations of the invention are possible in light of the above teachings, and therefore the invention may be practiced otherwise than as particularly described.

What is claimed is:

1. A method of treating migrainous headaches, comprising administering an aqueous composition consisting essentially of feverfew extract and ginger extract sublingually to a patient in need thereof in a total administered amount of from about 4 mg to about 40 mg of feverfew extract in a two hour period.

2. The method of claim 1, wherein said total administered amount is from about 4 mg to about 20 mg of feverfew extract in a two hour period.

3. The method of claim 1, wherein said the feverfew extract has a standardized parthenolide concentration of from about 1.2% to about 10%.

4. The method of claim 1, wherein said composition additionally comprises a mucosal permeation enhancer.

5. The method of claim 1, wherein said composition has a pH of from about 2 to about 6.

6. The method of claim 1, wherein said composition has a pH of from about 3.0 to about 6.0.

7. The method of claim 1, wherein said composition further comprises 0.05–5% ascorbic acid and 0.05–5% sodium lauryl sulfate.

8. The method of claim 7, wherein said total administered amount is divided among a plurality of compositions, and said plurality of compositions are administered sequentially.

9. The method of claim 1, wherein said composition is held sublingually for at least about 30 seconds prior to swallowing.

10. The method of claim 1, wherein said composition is circulated about the mouth prior to swallowing.

11. A method of treating migrainous headaches, comprising administering an aqueous composition consisting essentially of feverfew extract and ginger extract sublingually to a patient in need thereof in a total administered amount of from about 4 mg to about 40 mg of feverfew extract in a 24 hour period.

12. The method of claim 11, wherein the feverfew extract is administered in at least two doses, and wherein each individual dose of feverfew extract does not exceed about 10 mg.

* * * * *